United States Patent [19] [11] 3,993,672
Arzoumanian et al. [45] Nov. 23, 1976

[54] PROCESS FOR DIRECT OLEFIN OXIDATION

[75] Inventors: Henri Arzoumanian; Alain A. Blanc, both of Marseille, France; Ulrich Hartig, Neckargmund, Germany; Jacques V. Metzger, Marseille, France

[73] Assignee: Agence Nationale de Valorisation de la Recherche (ANVAR), Neuilly-sur-Seine, France

[22] Filed: Aug. 21, 1974

[21] Appl. No.: 499,174

[30] Foreign Application Priority Data
Sept. 7, 1973  Germany.......................... 7332327

[52] U.S. Cl. ...................... 260/348.5 V; 260/617 H
[51] Int. Cl.² ...................................... C07D 301/06
[58] Field of Search ............................. 260/348.5 V

[56] References Cited
FOREIGN PATENTS OR APPLICATIONS
| | | |
|---|---|---|
| 1,505,337 | 11/1967 | France ........................ 260/348.5 V |
| 1,506,303 | 11/1967 | France |
| 1,572,146 | 5/1969 | France ........................ 260/348.5 V |
| 1,280,234 | 10/1968 | Germany .................... 260/348.5 V |
| 46-42089 | 12/1971 | Japan |
| 1,201,086 | 8/1970 | United Kingdom .......... 260/348.5 V |
| 1,206,166 | 9/1970 | United Kingdom .......... 260/348.5 V |

OTHER PUBLICATIONS
E. S. Gould et al., Journal of Catalysis, vol. 13 (1969), pp. 238–244.

Primary Examiner—Norma S. Milestone
Attorney, Agent, or Firm—Brooks Haidt Haffner & Delahunty

[57] ABSTRACT

Olefins containing from 3 to 30 carbon atoms are directly oxidized to epoxides and allyl alcohols in the liquid phase by contact with a gas stream comprising oxygen but substantially free from hydrogen, in the presence of two metal compound catalysts which are soluble in the reaction mixture. The catalysts are preferably a compound of a Group VII or VIII metal and a compound of a Group VA or VIA transition metal.

16 Claims, 3 Drawing Figures

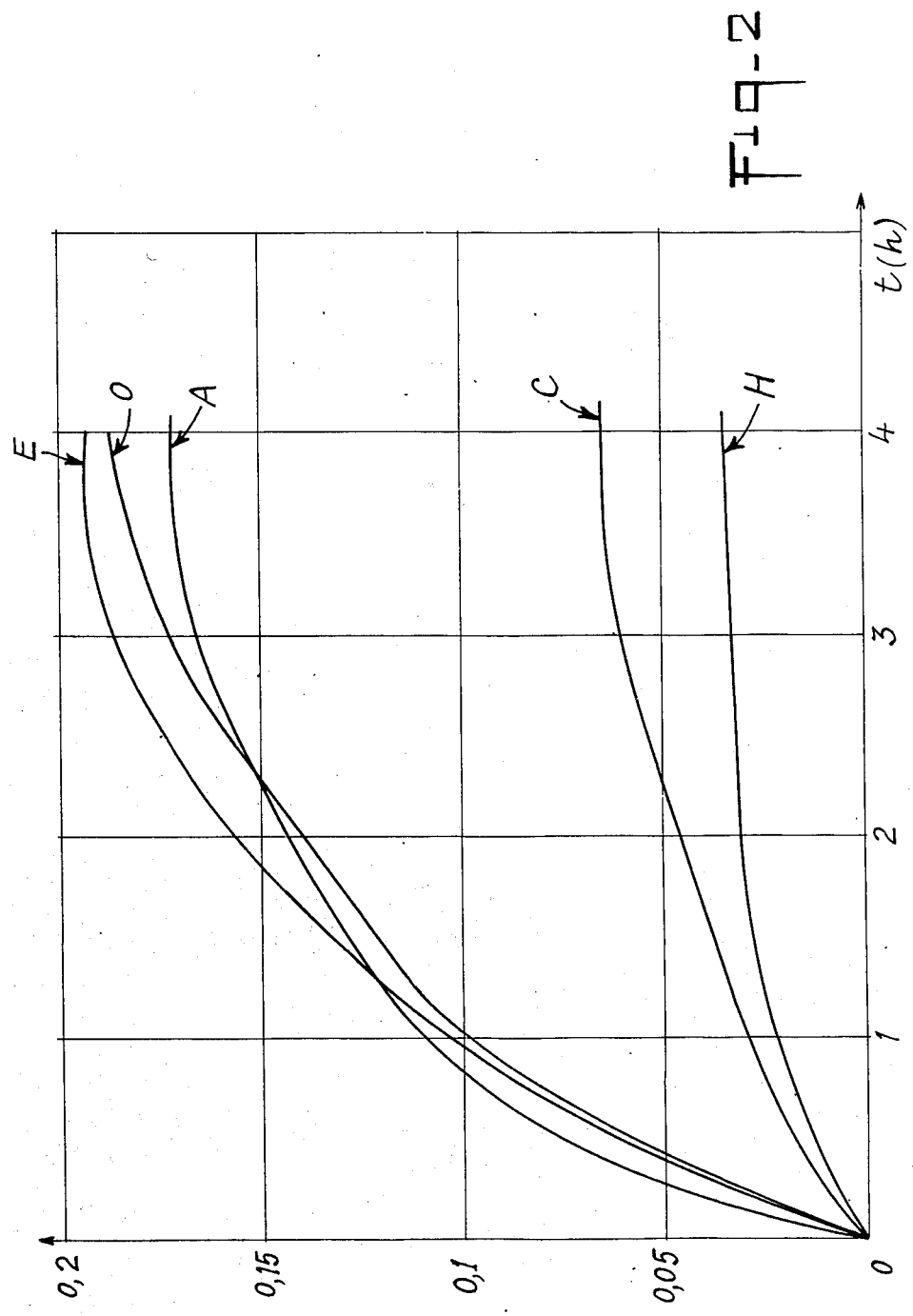

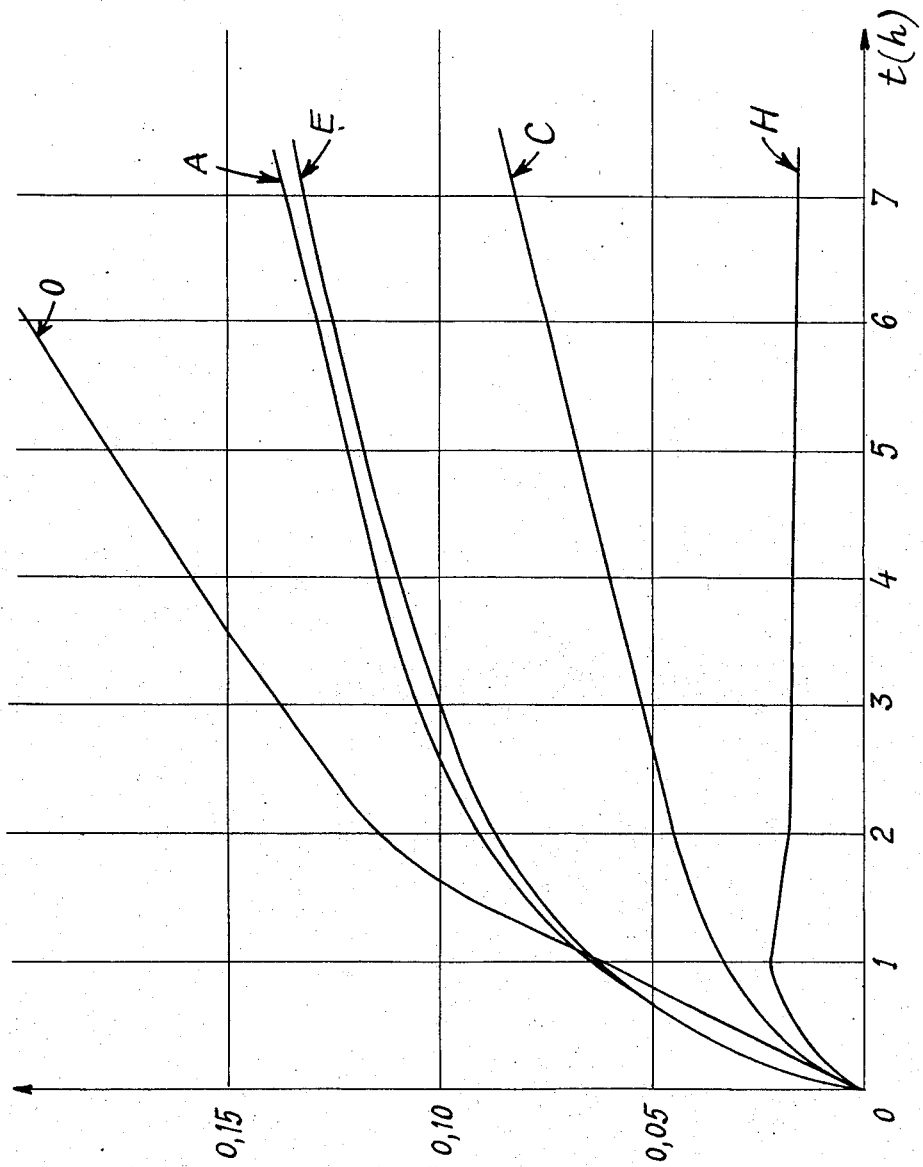

PROCESS FOR DIRECT OLEFIN OXIDATION

The present invention relates to a process for oxidising olefins containing 3 to 30 carbon atoms to form both epoxides and allyl alcohols.

Certain known processes for the epoxidation of olefins comprise two separate reaction steps, the first of which is the reaction leading to the formation of the hydroperoxide, and the second of which is that involving the conversion of the hydroperoxide to the epoxide. The starting materials are either the olefin alone, or the olefin together with a hydroperoxide or an aldehyde. In the former case, the oxidation is brought about by hydrogen peroxide in the presence of catalysts which may be either organic or inorganic. When organic catalysts are used, at least one will possess an —OH group or a group which can generate an —OH group in the presence of $H_2O$ or $H_2O_2$, and the second will be a Mo, W, V, Se or B compound.

In some processes, two catalysts are used, one based on copper and the other on molybdenum. These catalysts are insoluble in the reaction mixture and the reactants are not kept in the liquid phase. In another process an organometallic complex, more particularly of platinum, and a silver complex are used, but this is only applicable in the oxidation of cyclic olefins.

There are other known processes for the oxidation of olefins to yield epoxides and unsaturated alcohols. For example, the oxidation can be effected using oxygen in the presence of a modybdate or tungstate, and using an ultra-violet lamp for the first radical-generating step.

In another process, developed to reduce the number of steps leading to epoxidation, it has been proposed to start from olefins alone in the liquid phase, and to introduce oxygen and hydrogen (in proportions of 1 litre of $H_2$ per 5 litres of air) in the presence of two catalysts, the first being either soluble or in the form of a metal on an inert support, and the second being a noble metal from group VIII, preferably Pd, in the free metal state, on a support consisting of a silica or alumina gel. This process has certain disadvantages. For example, the mixture of oxygen and hydrogen employed can explode. Moreover, compared with homogeneous catalysis, heterogeneous catalysis possesses disadvantages well known to those skilled in the art, one of which is the formation, during the reaction, of large amounts of water which must be removed continuously in order to prevent hydrolysis of the epoxidised end-products. The concentration of water must not exceed 10% of the weight of the liquid phase. Moreover, the yield of epoxide is not very good, e.g. $10^{-3}$ mol of 1,2-epoxy-octane is produced per hour from 30 grams of 1-octene.

Among the solvents used are aliphatic, aromatic and naphthenic hydrocarbons, in particular toluene and alcohols, but the choice is narrow because certain solvents also undergo oxidation under the reaction conditions employed.

We have now devised a process for the direction oxidation of olefins to epoxides and allyl alcohols by homogeneous catalysis in the liquid phase, by which good yields of the derived products can be obtained.

According to the invention, there is provided a process for oxidising an olefin, containing from 3 to 30 carbon atoms, to form an epoxide and an allyl alcohol, which comprises contacting a liquid phase comprising the said olefin and having dissolved therein at least two metal catalysts for the oxidation, with a gas which contains oxygen and is substantially free from hydrogen.

In the process of the invention, one catalyst (hereinafter termed "the first catalyst") is desirably a compound of a metal of group VII or VIII of the Periodic Table, and the other catalyst (hereinafter termed "the second catalyst") is desirably a compound of a transition metal of group VA or VI A of the Periodic Table.

The first catalyst is preferably a compound of one of the following metals: iron, platinum, cobalt, rhodium, iridium and nickel; and the second catalyst is preferably a compound of one of the following metals: molybdenum, tungsten, vanadium, niobium, titanium and manganese.

Among the most preferred two-metal catalyst systems are the following:

a combination of iron triacetylacetonate, platinum diacetylacetonate, aqueous nickel diacetylacetonate, cobalt triacetylacetonate, chlorocarbonyl-bis-(triphenylphosphine)-iridium, chloro-tris-(triphenylphosphine)-rhodium, rhodium triacetylacetonate or chlorocarbonyl-bis-(triphenylphosphine)-rhodium, with molybdenum oxodiperoxaquohexamethylphosphorotriamide;

a combination of aqueous nickel diacetylacetonate, cobalt triacetylacetonate, chlorocarbonyl-bis-(triphenylphosphine)-iridium or chloro-tris-(triphenylphosphine)-rhodium, with vanadium triacetylacetonate;

a combination of chloro-tris-(triphenylphosphine)-rhodium with tungstic acid, molybdenum triacetylacetonate, niobium pentaethylate, manganese diacetylacetonate or titanium oxyacetylacetonate;

a combination of chlorocarbonyl-bis-(triphenylphosphine)- rhodium with molybdenum pentacarbonyl; and a combination of rhodium triacetylacetonate with molybdenum triacetylacetonate.

In the process of the invention, the liquid phase desirably comprises a solvent which does not readily undergo oxidation. Preferably, the solvent is carbon tetrachloride, benzene, nitrobenzene, dinitrobenzene, chlorobenzene, dichlorobenzene or fluorobenzene). Solvents containing a readily oxidisable group, e.g. ethanol and methanol, cannot be used.

A minute amount of a radical reaction initiator is also used. This makes it possible to trigger the oxidation reaction more quickly and thus to reduce the duration of the reaction. Preferably, the initiator is an azo compound, such as $\alpha,\alpha'$-azoisobutyronitrile, or benzoyl peroxide or hydroperoxide. Tetriary butyl hydroperoxide or cumyl hydroperoxide may also optionally be used.

Preferably, the conditions under which the process is carried out are chosen so that the partial pressure of oxygen is from above 100 millibars but below the flash point of the reaction mixture, and the reaction temperature is below the boiling point of the said olefin at the pressure at which the reaction is carried out. When the pressure is 1 atmosphere, the temperature is preferably between 25° C and 150° C.

When cyclohexene is used as the olefin and is present at a concentration of 4.88 mols/l and chloro-tris-(triphenylphosphine)-rhodium at a concentration of between 1 and $2 \times 10^{-3}$ mol/l and molybdenum oxodiperoxaquohexamethylphosphorotriamide at a concentration, expressed in mols/l, $0.5 \times 10^{-3}$ mol/l greater than that of the first catalyst are used as the catalyst mixture, and when nitrobenzene is used as the solvent and tertiary butyl hydroperoxide, at a concentration of $10^{-2}$ mol/l is used as the initiator, and the temperature is raised to 70° C for 150 minutes under an oxygen pressure of one atmosphere, then 44 mol% of epoxide and a yield, expressed in mols, of allyl alcohol of between 42 and 44% are obtained.

The process of the invention results in the conjoint production of epoxides and allyl alcohols. The process is simpler than prior art processes, in that a single reactor is required, the catalysis is homogeneous in the liquid phase (and it is not necessary, therefore, continuously to remove water formed during the reaction as it would be in heterogeneous catalysis).

Another advantage of the process of the invention is that the gas mixture used contains oxygen but no hydrogen, and therefore no explosive oxygen/hydrogen mixture is involved.

Furthermore, the fact that the reaction is carried out in a homogeneous liquid phase makes it possible to achieve better physical absorption and other advantages well known to those skilled in the art.

Many of the two-metal systems which may be used as catalysts in the process are relatively inexpensive and easily available materials.

In order that the invention may be more fully understood, various Examples are given below by way of illustration only. In the accompanying drawings:

FIG. 2 represents the selectivity in mol/litre of products obtained in Example 15.

FIG. 3 represents the selectivity in mol/litre of products obtained in Example 18.

Figure 1:
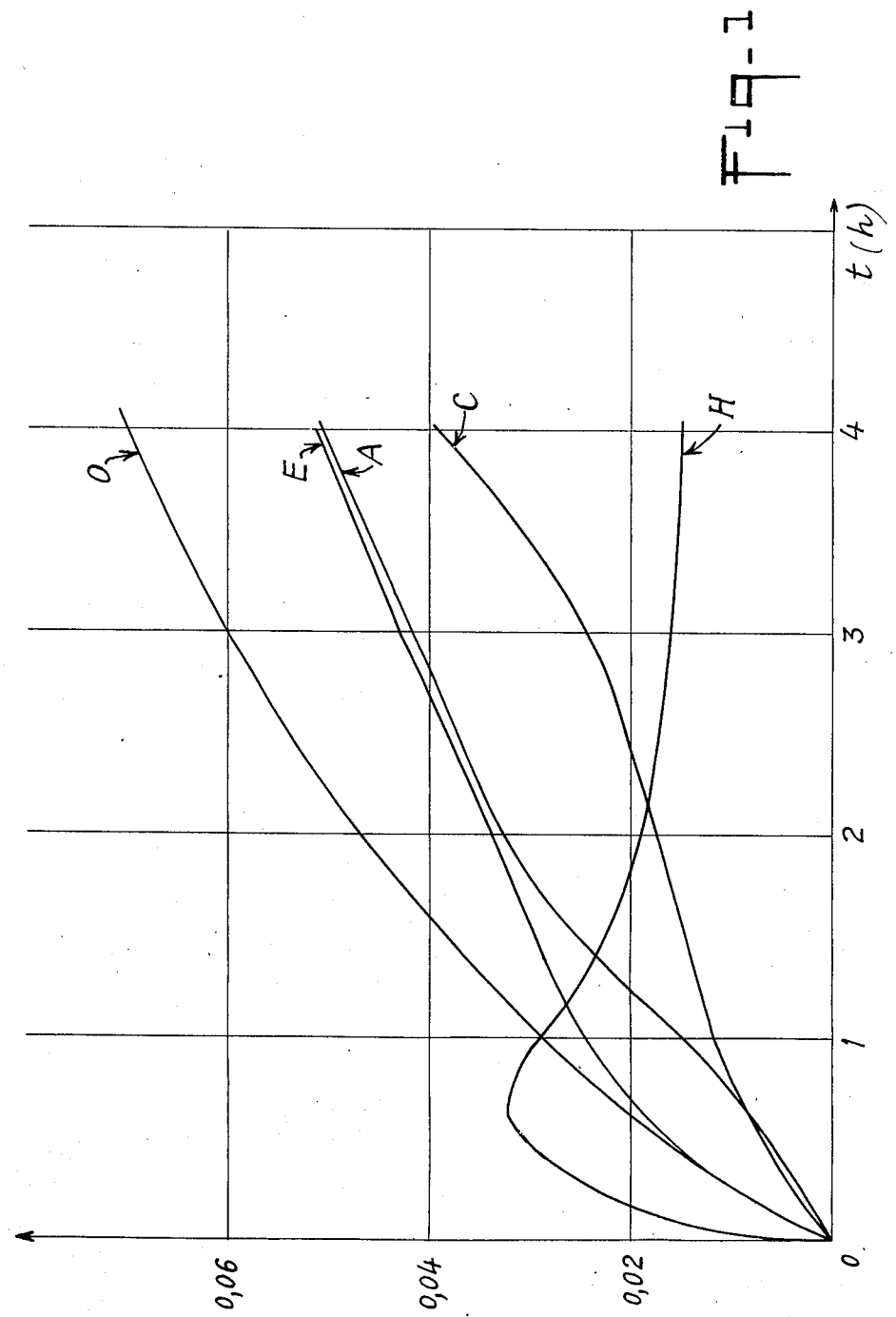
FIG. 1 represents the selectivity in mol/litre of products obtained in Example 13.

It is to be noted that the term "compound" applies both to a complex and to an acid or a salt.

EXAMPLES 1 to 10

In all these Examples, the following procedure was used:

A thermostatically-controlled reactor was used which was equipped with an efficient stirring device, a thermometer, a dip tube for introducing oxygen and a system for removing samples. The oxygen was supplied from a graduated Mariotte vessel, which made it possible to measure the consumption of oxygen with time. The operations were carried out at atmospheric pressure and at a temperature which varied, depending on the particular experiments, from 50° to 135° C.

The solvent, the catalysts, the olefin and the initiator, which was tertiary butyl hydroperoxide or cumyl hydroperoxide at a concentration of $10^2$ mol/litre, were introduced into the reactor. The reactor was placed in the thermostatically-controlled bath and stirring was started. When the chosen temperature was reached, the introduction of oxygen was begun. When the desired period of time had passed, a sample of the reaction mixture was removed and the hydroperoxides were measured by iodometry, and the other products resulting from the oxidation were measured by vapour phase chromatography.

The results obtained are set out in the Table below, where the concentrations of the reagents and catalysts are expressed in mols per litre.

The extent of the reaction is expressed in mols of oxygen consumed per mole of olefin.

The selectivities with respect to the reaction products are expressed in mol%.

EXAMPLE 11

Propene was used as the olefin. A 250 ml reactor was employed, into which 40 to 50 ml of benzene (as solvent) and 40 g of propene under a pressure of 30 bars, were introduced. The catalyst system employed consisted of the following compounds:

$RhCl(PPh_3)_3$ at a concentration of between 0.18 and $1.5 \times 10^{-3}$ mol/litre, and $MoO_5 \cdot HMPT \cdot H_2O$ at a concentration of between 0.15 and $1.5 \times 10^{-3}$ mol/litre.

The pressure was then incresed to 50 bars.

Air was used as the gas mixture and was conveyed to the reactor through a dip tube. The air was bubbled in under pressure when the temperature was between 90° and 110° C, the reactor being in a thermostatically controlled bath, and after having started the stirring. The initiator used was azoisobutyronitrile at a concentration of up to 0.02 mol/litre of solution.

A sample was removed in order to measure the hydroperoxides by iodometry and the other products resulting from the oxidation by gas phase chromatography.

The results were as follows:

$$\text{If } \left[\frac{Mo}{Rh}\right] = \frac{1.5}{1.5},$$

the ratio:

$$\frac{\text{Epoxide obtained (+ products originating from the epoxide)}}{\text{Allyl alcohol obtained (+ products originating from allyl alcohol)}} = 1,$$

at T = 110° C.

EXAMPLES 12 to 27

In all these Examples, the reactions were carried out in a thermostatically-controlled 200 ml glass reactor equipped with a dropping funnel, a thermometer, a partition, a condenser, a tube dipping to the bottom of the reactor for introducing oxygen, and a magnetic stirrer. The procedure was the same in all these Examples and was as follows:

48 ml of nitrobenzene (solvent) followed by $2 \times 10^{-3}$ mol/l of each catalyst of the two-metal catalyst system chosen, were placed under oxygn.

50 ml (equivalent to 0.5 mol of pure distilled cyclohexene) of a solution of concentration 5 mols/l, and, on the other hand, 90 mg of a solution of tertiary butyl hydroperoxide of concentration $10^{-2}$ mol/l were added at 60° C, whilst stirring slowly. Absorption of oxygen, which was supplied from a graduated flask, began when stirring of the solution was speeded up. The rate of absorption was noted at atmospheric pressure.

All the Examples were carried out using a minute dose of a radical initiator, in order to accelerate the production of epoxides and allyl alcohols. It is emphasised that this initiator is not essential and need not be present in the reaction mixture.

In the processes of the Examples, the working conditions were as follows. The temperature was chosen between 25° C and 150° C and was in any event below the boiling point of the olefin at the particular pressure employed. The pressure was such that the olefin was in the liquid phase. If the pressure were increased, it would then have been possible to lower the temperature. The partial pressure of oxygen was preferably equal to, or above, 100 mm Hg.

If these conditions were not fulfilled, the rate of reaction was slower. The gas mixture had to be sufficiently rich in oxygen, although there was an upper limit for the pressure in order to avoid reaching the flask point of the reaction mixture. It was necessary that the partial pressures of oxygen and olefin should not exceed certain values in the presence of metals.

The first of the two catalysts forming the two-metal system was chosen from the compounds of metals from groups VII and VIII and the second was chosen from compounds of transition metals from groups V A and VI A. It was absolutely necessary that these compounds should be soluble in the reaction mixture. The metal compounds used in the Examples, were: compounds of Fe, Co, Ni, Rh, Pt and Ir, with compounds of Mo, W, V, Nb, Mn and Ti.

The catalyst systems which combine a cobalt compound and a vanadium compound are particularly valuable because they are very substantially less expensive than catalyst systems of rhodium and molybdenum compounds.

The results obtained in Examples 1 to 10 and 12 to 27 are given in the Tables below.

The catalyst systems consisted of a mixture of two catalysts denoted in the Tables below according to the following key:

II — Molybdenum oxodiperoxaquohexamethylphosphorotriamide
III — Rhodium triacetylacetonate
IV — Molybdenum triacetylacetonate
V — Aqueous nickel diacetylacetonate
VI — Vanadium triacetylacetonate
VII — Cobalt triacetylacetonate
VIII — Chlorocarbonyl-bis-(triphenylphosphine)-iridium
IX — Tungstic acid
X — Chlorocarbonyl-bis-(triphenylphosphine)-rhodium
XI — Molybdenum pentacarbonyl
XII — Iron triacetylacetonate
XIII — Platinum diacetylacetonate
XIV — Niobium pentaethylate
XV — Titanium oxyacetylacetonate
XVI — Manganese diacetylacetonate.

The letters E, A, K and H are, respectively, abbreviations for epoxides, allyl alcohols, ketones and hydroperoxides.

In the accompanying drawings, FIGS. 1, 2 and 3 correspond respectively to Examples 13, 15 and 18 and are graphs whereon the time which has passed in hours is plotted as the abscissae, and the number of mols per litre of, respectively, epoxides in the case of graph E, allyl alcohols in the case of graph A, hydroperoxides in the case of graph H and ketones in the case of graph K, as well as the number of mols per litre of $O_2$ absorbed and divided by 3 in the case of graph O, are plotted as the ordinates.

| Exp. | olefin | Concentration (mol/l) of olefin | Solvent | 1st catalyst | Concentration (mol/l) | 2nd catalyst | Concentration (mol/l) | Temperature °C | Duration (minutes) | Extent of reaction (mol of $O_2$/mol of olefin) | Selectivity in mol % | | | |
|---|---|---|---|---|---|---|---|---|---|---|---|---|---|---|
| | | | | | | | | | | | E | A | K | H |
| 1 | Cyclohexene | 4.88 | Nitrobenzene | I | $2 \times 10^{-3}$ | II | $1.5 \times 10^{-3}$ | 50° | 150 | 0.10 | 37 | 37 | 9 | 18 |
| 2 | " | " | " | " | " | " | $2.5 \times 10^{-3}$ | 70° | " | 0.09 | 44 | 42 | 9 | 3 |
| 3 | " | " | " | " | $1 \times 10^{-3}$ | " | $1.5 \times 10^{-3}$ | " | " | 0.04 | 44 | 44 | 5 | 5 |
| 4 | 1-Hexene | " | " | " | $2 \times 10^{-3}$ | " | " | 60° | 570 | 0.10 | 32 | 32 | 16 | 20 |
| 5 | Cyclohexene | " | Benzene | III | $2 \times 10^{-3}$ | IV | $1.5 \times 10^{-3}$ | 50° | 150 | 0.09 | 43 | 43 | 7 | 5 |
| 6 | " | " | " | I | $2 \times 10^{-3}$ | IV | $2.5 \times 10^{-3}$ | 70° | " | 0.09 | 44 | 43 | 8 | 4 |
| 7 | 1-Octene | 2.0 | Nitrobenzene | XII | $2 \times 10^{-3}$ | II | $1.3 \times 10^{-3}$ | 100° | 300 | 0.10 | 34 | 52 | | 12 |
| 8 | 1-Decene | 2.0 | " | XII | $1 \times 10^{-3}$ | II | $1 \times 10^{-3}$ | 100° | 480 | 0.23 | 35 | 50 | 13 | 2 |
| 9 | 1-Eicosene | 1.78 | " | XII | $1 \times 10^{-3}$ | II | $1 \times 10^{-3}$ | 100° | 480 | 0.33 | 40 | 48 | 10 | 2 |
| 10 | 1-Eicosene | 1.78 | " | XII | $1 \times 10^{-3}$ | II | $1 \times 10^{-3}$ | 135° | 120 | 0.30 | 36 | 50 | 12 | 2 |

SELECTIVITY IN MOL % OF EPOXIDE

| Duration (hours) | Ex. 12 V+II | Ex. 13 V+VI | Ex. 14 VII+II | Ex. 15 VII+V | Ex. 16 VIII+II | Ex. 17 VIII+V | Ex. 18 I+V | Ex. 19 I+IX | Ex. 20 III+II | Ex. 21 X+II | Ex. 22 X+XI |
|---|---|---|---|---|---|---|---|---|---|---|---|
| 1 | 34.3 | 30.9 | 19.2 | 38.6 | 10.9 | 21.9 | 35.4 | 4.2 | 15.1 | 11.3 | 3.9 |
| 2 | 43.3 | 32.4 | 30.0 | 41.5 | 14.0 | 22.8 | 36.8 | 3.6 | 21.0 | 8.5 | 8.9 |
| 3 | 59.1 | 35.4 | 30.9 | 42.1 | 16.6 | 23.8 | 36.5 | 2.9 | 23.7 | 5.2 | 6.3 |
| 4 | 62.3 | 32.0 | 28.9 | 41.7 | 20.2 | 24.0 | 36.4 | 5.6 | 27.0 | 27.2 | 24.0 |

| | Ex. 23 XIII+II | Ex. 24 XIII+II | Ex. 25 I+XIV | Ex. 26 I+XV | Ex. 27 I+XVI |
|---|---|---|---|---|---|
| 1 | 30 | 54 | 19 | 18 | 4 |
| 2 | 38 | 50 | 19 | 14 | 2 |
| 3 | 42 | 47 | 12 | 13 | 4 |
| 4 | 40 | 47 | 10 | 12 | 6 |

I — Chloro-tris-(triphenylphosphine)-rhodium

SELECTIVITY IN MOL % OF ALLYL ALCOHOL

| Duration | Ex. 12 | Ex. 13 | Ex. 14 | Ex. 15 | Ex. 16 | Ex. 17 | Ex. 18 | Ex. 19 | Ex. 20 | Ex. 21 | Ex. 22 |

-continued

| (hours) | V+II | V+VI | VII+II | VII+V | VIII+II | VIII+V | I+V | I+IX | III+II | X+II | X+XI |
|---|---|---|---|---|---|---|---|---|---|---|---|
| | \multicolumn{11}{c}{SELECTIVITY IN MOL % OF ALLYL ALCOHOL} |
| 1 | 0.0 | 18.5 | 4.1 | 41.7 | 10.0 | 29.7 | 34.8 | 8.1 | 10.8 | 0.0 | 0.0 |
| 2 | 7.5 | 32.4 | 21.4 | 38.3 | 13.8 | 30.8 | 37.7 | 12.3 | 9.9 | 1.3 | 8.0 |
| 3 | 13.9 | 33.1 | 29.6 | 37.4 | 18.7 | 33.0 | 38.8 | 15.0 | 11.5 | 16.7 | 16.9 |
| 4 | 19.3 | 32.7 | 44.5 | 37.1 | 28.2 | 35.1 | 38.4 | 7.0 | 14.6 | 17.3 | 17.4 |

| | Ex. 23 XII+II | Ex. 24 XIII+II | Ex. 25 I+XIV | Ex. 26 I+XV | Ex. 27 I+XVI |
|---|---|---|---|---|---|
| 1 | 30 | 39 | 3 | 9 | 25 |
| 2 | 31 | 38 | 5 | 2 | 32 |
| 3 | 32 | 41 | 5 | 1 | 20 |
| 4 | 36 | 47 | 5 | 1 | 13 |

| Duration (hours) | Ex. 12 V+II | Ex. 13 V+VI | Ex. 14 VII+II | Ex. 15 VII+V | Ex. 16 VIII+II | Ex. 17 VIII+V | Ex. 18 I+V | Ex. 19 I+IX | Ex. 20 III+II | Ex. 21 X+II | Ex. 22 X+XI |
|---|---|---|---|---|---|---|---|---|---|---|---|
| | \multicolumn{11}{c}{SELECTIVITY IN MOL % OF KETONE} |
| 1 | 1.5 | 14.8 | 34.3 | 11.4 | 20.7 | 25.1 | 18.0 | 7.2 | 17.3 | 7.2 | 9.9 |
| 2 | 1.4 | 17.7 | 17.3 | 12.0 | 23.3 | 28.6 | 18.4 | 19.2 | 17.6 | 11.8 | 18.9 |
| 3 | 1.1 | 18.5 | 15.9 | 13.4 | 24.2 | 31.3 | 18.8 | 19.5 | 18.4 | 18.9 | 16.9 |
| 4 | 0.9 | 25.5 | 14.2 | 14.9 | 21.6 | 33.1 | 19.9 | 26.3 | 17.8 | 13.9 | 14.7 |

| | Ex. 23 XII+II | Ex. 24 XIII+II | Ex. 25 I+XIV | Ex. 26 I+XV | Ex. 27 I+XVI |
|---|---|---|---|---|---|
| 1 | 0 | 0 | 11 | 15 | 29 |
| 2 | 6 | 6 | 10 | 14 | 30 |
| 3 | 5 | 6 | 12 | 15 | 28 |
| 4 | 4 | 6 | 14 | 16 | 28 |

We claim:

1. A process for oxidising an olefin containing from 3 to 30 carbon atoms to form an epoxide and an allyl alcohol, which process comprises forming a solution of the olefin in an organic solvent which is not oxidised under the reaction conditions, dissolving in the solution a first catalyst which is a soluble compound of rhodium, and a second catalyst which is a soluble compound of molybdenum, tungsten, vanadium, niobium, titanium, and manganese which together catalyse the oxidation of the olefin, and contacting the catalyst-containing solution so formed with a gas which includes oxygen but is free from hydrogen, until substantial quantities of the epoxide and the allyl alcohol have been formed.

2. A process for oxidizing an olefin containing from 3 to 30 carbon atoms to form an epoxide and an allyl alcohol, which process comprises forming a liquid phase containing the reactants and a non-oxidizable solvent having dissolved therein the said olefin, a first soluble metal catalyst and a second soluble metal catalyst for the reaction, the first metal catalyst being a soluble compound of rhodium, and the second metal catalyst being a soluble compound of a metal selected from molybdenum, tungsten, niobium, titanium, manganese, and vanadium, and contacting the liquid phase with a gas which contains oxygen and is substantially free from hydrogen, at temperature which is below the boiling point of the olefin under the reaction conditions.

3. A process according to claim 2 wherein the molar concentrations of the two catalysts are, respectively, in the ratio of about 0.7 to about 1.5.

4. A process according to claim 2, wherein the first catalyst is selected from aqueous chloro-tris-(triphenylphosphine)-rhodium, rhodium triacetylacetonate, chlorocarbonyl-bis-(triphenylphosphine)-rhodium, and the second catalyst is selected from molybdenum oxodiperoxaquohexamethylphosphorotriamide, vanadium triacetylacetonate, tungstic acid, molybdeum triacetylacetonate, molybdenum pentacarbonyl, niobium pentaethylate, manganese diacetylacetonate and titanium acetylacetonate.

5. A process according to claim 2, wherein the first catalyst is selected from aqueous chloro-tris-(triphenylphosphine)-rhodium, rhodium triacetylacetonate, chlorocarbonylbis-(triphenylphosphine)-rhodium, and second catalyst is molybdenum oxodiperoxaquohexamethylphosphorotriamide.

6. A process according to claim 2, wherein the first catalyst is aqueous chloro-bis-(triphenylphosphine)-rhodium, and the second catalyst is vanadium triacetonacetonate.

7. A process according to claim 2, wherein the first catalyst is chloro-tris-(triphenylphosphine)-rhodium, the second catalyst is selected from tungstic acid, niobium pentaethylate, manganese diacetylacetonate, titanium acetylacetonate and molybdenum triacetylacetonate, 8. A process according to claim 2, wherein the first catalyst is rhodium triacetylacetonate, and the second catalyst is molybdenum triacetylacetonate.

9. A process according to claim 2, wherein the first catalyst is chlorocarbonyl-bis-(triphenylphosphine)-rhodium, and the second catalyst is molybdenum pentacarbonyl.

10. A process according to claim 1, wherein the solvent is selected from carbon tetrachloride, benzene, nitrobenzene, dinitrobenzene, chlorobenzene and fluorobenzene.

11. A process according to claim 2, wherein the liquid phase also comprises a minute dose of a radical reaction initiator.

12. A process according to claim 11, wherein the said initiator is selected from azo compounds, benzoyl peroxide and hydroperoxide, tertiary butyl hydroperoxide, and cumyl hydroperoxide.

13. A process according to claim 11 wherein the initiator α,α'-azoisobutyronitrile.

14. A process according to claim 2 wherein during contact of the liquid phase with the gas, the oxygen partial pressure is below flash point of the liquid phase but above 100 millibars, and the temperature is below the boiling point of the said olefin under the reaction conditions.

15. A process according to claim 14, wherein the temperature is between 25° C and 150° C and the reaction is carried out at atmospheric pressure.

16. A process according to claim 2 wherein the olefin is cyclohexene, the cyclohexene being present in the liquid phase at a concentration of 4.88 mols/litre, and wherein the first catalyst is chloro-tris-(triphenylphosphine)-rhodium at a concentration of from 1 to 2 × $10^{-3}$ mol/litre, and the second catalyst is molybdenum oxodiperoxaquohexamethylphosphorotriamide at a concentration $0.5 \times 10^{-3}$ mol/litre greater than the said first catalyst, and wherein the liquid phase comprises nitrobenzene as solvent and tertiary butyl hydroperoxide at a concentration of $10^{-2}$ mol/litre as an initiator, and wherein the temperature is raised to 70° C under an oxygen pressure of 1 atmosphere and, after 150 minutes, 44 mol% of epoxide and a molar percentage of allyl alcohol of between 42 and 44% are obtained.

* * * * *

UNITED STATES PATENT AND TRADEMARK OFFICE
CERTIFICATE OF CORRECTION

PATENT NO. : 3,993,672
DATED : November 23, 1976
INVENTOR(S) : HENRI ARZOUMANIAN ET AL It is certified that error appears in the above-identified patent and that said Letters Patent are hereby corrected as shown below:

First page, Item "[30]", "Germany" should read --France--.

Column 2, line 42, cancel parenthesis sign after "fluorobenzene"; Column 2, line 50, correct the spelling of "Tertiary".

Column 3, line 56, "$10^2$" should read --$10^{-2}$--.

Column 4, line 51, correct the spelling of "oxygen".

Column 5, line 9, "flask" should read --flash--; Column 5, second table, under "Ex. 23", "XIII" should read --XII--.

Column 8, line 31, correct the spelling of "molybdenum"; Column 8, line 38, "chlorocarbonylbis" should be --chlorocarbonyl-bis--.

Column 9, line 2, after "initiator" insert --is--.

Signed and Sealed this twenty-sixth Day of July 1977

[SEAL]

Attest:

RUTH C. MASON
*Attesting Officer*

C. MARSHALL DANN
*Commissioner of Patents and Trademarks*